US006553988B1

(12) United States Patent
Holroyd

(10) Patent No.: US 6,553,988 B1
(45) Date of Patent: Apr. 29, 2003

(54) MEDICAMENT DISPENSING DEVICE WITH A MULTIMATERIAL DIAPHRAGM BOUNDING A PNEUMATIC FORCE CHAMBER

(75) Inventor: Michael John Holroyd, Great Shetford (GB)

(73) Assignee: Norton Healthcare, Inc., London (GB)

( * ) Notice: Subject to any disclaimer, the term of this patent is extended or adjusted under 35 U.S.C. 154(b) by 77 days.

(21) Appl. No.: 09/591,321

(22) Filed: Jun. 9, 2000

(51) Int. Cl.[7] .............................................. A61M 11/00
(52) U.S. Cl. ............................ 128/200.23; 128/200.14; 128/203.12
(58) Field of Search ....................... 128/200.14, 200.23, 128/200.18, 203.12, 203.15; 267/158, 149, 148

(56) References Cited

U.S. PATENT DOCUMENTS

| 3,456,645 | A | * | 7/1969 | Brock ................... 128/200.23 |
| 3,506,004 | A | * | 4/1970 | Mann et al. ........... 128/200.23 |
| 3,565,070 | A | * | 2/1971 | Hanson et al. ......... 128/200.23 |
| 3,598,294 | A | * | 8/1971 | Hedrick et al. ......... 222/402.2 |
| 3,702,114 | A | * | 11/1972 | Zacarian ................ 128/200.23 |
| 3,789,843 | A | * | 2/1974 | Armstrong et al. .... 128/200.23 |
| 4,414,972 | A | * | 11/1983 | Young et al. ........... 128/200.23 |
| 4,648,393 | A | * | 3/1987 | Landis et al. .......... 128/200.23 |
| 5,027,808 | A | * | 7/1991 | Rich et al. ............. 128/200.23 |
| 5,069,204 | A | * | 12/1991 | Smith et al. ........... 128/200.23 |
| 5,119,806 | A | * | 6/1992 | Palson et al. .......... 128/200.14 |
| 5,184,761 | A | * | 2/1993 | Lee ........................ 128/200.23 |
| 5,217,004 | A | * | 6/1993 | Blasnik et al. .......... 128/200.14 |
| 5,224,472 | A | * | 7/1993 | Pesenti et al. .......... 128/200.14 |
| 5,447,150 | A | * | 9/1995 | Bacon ..................... 128/200.14 |
| 5,772,190 | A | * | 6/1998 | May et al. ................. 267/141 |
| 6,189,904 | B1 | * | 2/2001 | Gentry et al. .......... 280/124.175 |
| 6,354,577 | B1 | * | 3/2002 | Quintile et al. .............. 267/149 |

FOREIGN PATENT DOCUMENTS

| GB | 1269811 A | 4/1972 |
| GB | 2263873 A | 8/1993 |
| GB | 2264238 A | 8/1993 |
| GB | 2344534 A | 6/2000 |
| WO | WO 93/24167 | * 12/1993 |

* cited by examiner

Primary Examiner—Aaron J. Lewis
Assistant Examiner—Mital Patel
(74) Attorney, Agent, or Firm—McDermott, Will & Emery

(57) ABSTRACT

A metered dose inhaler for use with a pressurized aerosol container which is preferably breath-actuated. A preload (80) is applied to the internal aerosol valve by an amount sufficient to result in a dose release, but this is prevented by the application of a pneumatic resisting force (130). The inhaler comprises a release device (110) which, upon actuation, releases the resisting force and allows the preload to actuate the aerosol valve (135). A metered dose of medicament is then released for inhalation by the patient. The pneumatic resisting force is established by a negative pressure region defined in part by a diaphragm. The diaphragm includes a central disk of a first, relatively high stiffness material and a peripheral ring, coupled by a flexure of a second, relatively low stiffness material.

7 Claims, 2 Drawing Sheets

Figure 1:
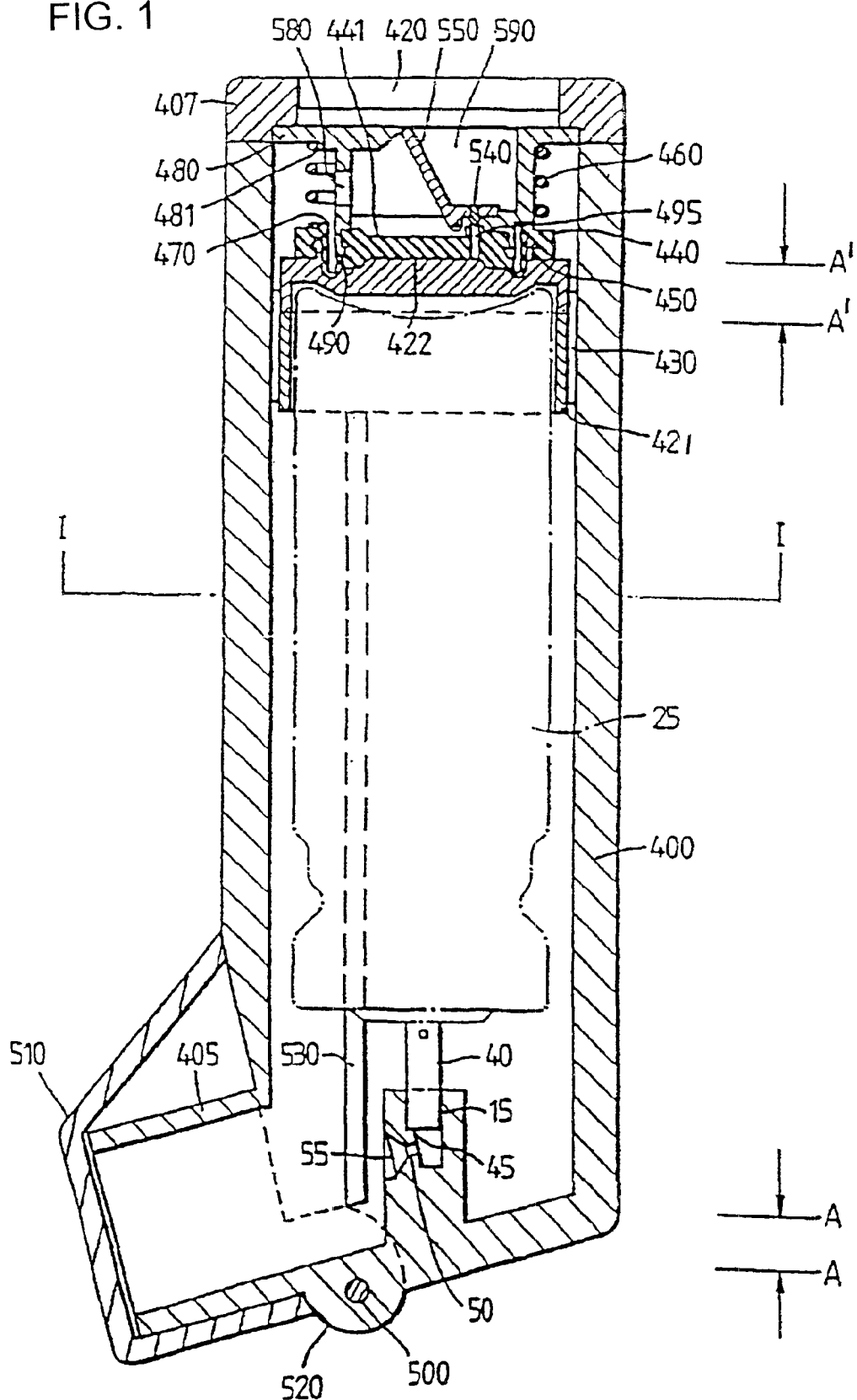
Figure 2:
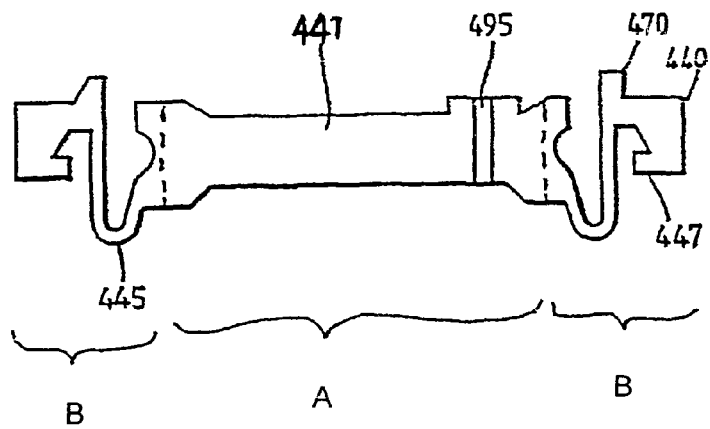

MEDICAMENT DISPENSING DEVICE WITH A MULTIMATERIAL DIAPHRAGM BOUNDING A PNEUMATIC FORCE CHAMBER

REFERENCE TO RELATED PATENT

The subject matter in this application is related to that in U.S. Pat. No. 5,447,150. That patent is incorporated by reference.

DESCRIPTION

1. Field of the Invention

This invention relates to a dispensing device, and more specifically, to a device suitable for dispensing discrete amounts of fluid.

In particular, the invention is concerned with a dispensing device of the type where the metered dose is administered in response to the inhalation of the patient.

2. Background of the Disclosure

Metered dose inhalers are well known in medicine for treatment, or alleviation of the effects of respiratory complaints, for example asthma. Breath-actuated devices are also known, and have been the subject of many patent applications.

GB 1288971; GB 1297993; GB 1335378; GB 1383761; GB 1392192; GB 1413285; WO85/01880; GB 2204799; U.S. Pat. No. 4,803,978 and EP 0186280A describe inhalation-actuated dispensing devices for use with a pressurised aerosol dispensing container. The device includes a dispensing container and the container includes a valve capable of releasing a metered amount of the aerosol contents, when an internal spring operating the valve is compressed by a sufficient amount. The dispensing device often comprises a chamber having a mouthpiece, air inlets, actuating means for causing the actuation of the valve in the dispensing container, a latching means for releasably retaining said metering valve in a charged position, and an inhalation responsive means for releasing the latch, such that a metered amount of aerosol compound is discharged into the region of the mouthpiece. The overall objective is to give co-ordination of discharge of medicament from the aerosol container with inhalation of the patient, thus allowing a maximum dose of medicament to reach the bronchial passages of the lungs.

The latching means is often connected to a valve which moves from a latching position to a dispensing position in response to a partial vacuum developed upon inhalation.

EP-A-0045419 describes an inhalation device having biassing means which are alone of insufficient force to depress the container but which together are of sufficient force to do so.

EP-A-186280 describes a device which employs magnets to control the release of the aerosol container.

U.S. Pat. No. 3,605,738 describes devices in which the aerosol container communicates with the mouthpiece via a metering chamber. A metered quantity of the aerosol compound is discharged into the metering chamber and this is conveyed to the mouthpiece via an inhalation-actuated valve.

GB 1269554 describes a device wherein the aerosol container is moveable by a lever and cam system into a charged position held by a latch, a pressure differential acting to trip the latch and move the valve of the container to a discharge position.

U.S. Pat. No. 5,447,150, incorporated by reference herein, disclosed a metered dose inhaler, wherein the release of the medicament is actuated by the inhalation of the patient. That patent disclosed an inhalation-actuated device which is more simple and compact than the then-prior art dispensers. In one disclosed form, a closed negative pressure region is defined in part by a diaphragm molded from a single material. The diaphragm includes a relatively thick central disk, surrounded by a relatively thin flexure and peripheral ring. That construction is difficult to fabricate, in part due to the differing thickness regions.

SUMMARY OF THE INVENTION

According to one aspect of the present invention there is provided an improved dispensing device for use with a drug delivery system comprising a means for releasing a measured dose of medicament from the system, the releasing means comprising a means for applying a preload capable of actuating the delivery means in the system, a means for applying a resisting pneumatic force capable of preventing actuation of the delivery means and a release device capable of freeing the resisting pneumatic force to allow the preload to actuate the delivery means and dispense the medicament. The means for applying a resisting pneumatic force of the present invention is similar to that in U.S. Pat. No. 5,447,550 but includes a structure that is distinct from, and provides substantial improvement over, the corresponding structure in U.S. Pat. No. 5,447,150.

The pneumatic resisting means of the present invention is provided by air which is held at a negative pressure below atmospheric prior to release. That negative pressure provides a pneumatic resisting force which opposes the preload force. The release device acts to return the pressure to atmospheric or prior equilibrium, thus allowing the full force of the preload to act. The pneumatic resisting force is established by a negative pressure region defined in part by a diaphragm. The diaphragm includes a central disk of a first, relatively high stiffness material and a peripheral ring, coupled by a flexure of a second, relatively low stiffness material. In various forms, the peripheral ring may be of the same material as the flexure, or may be of a different material.

The device is particularly suited for use with pressurized inhalation aerosols having valves as the delivery means.

Although this device has been described in particular relation to a system using air, it will be realized that in a closed system any suitable gas could be used.

In a preferred arrangement, there is provided a breath actuated dispensing device for use with an aerosol medicant container for dispensing a medicant in a metered dose. The container is cylindrical and extends along a container axis between a first end and a second end. The container has a spring based aerosol valve at the first end, which is responsive to an axial force above a predetermined threshold to release the metered dose. The device includes a housing disposed about a central axis and having a first end and a second end, where the second end includes a shoulder and an expulsion nozzle extending therethrough. A support sleeve is disposed within the housing. The sleeve is adapted for axial motion along the central axis. The sleeve is further adapted to support the second end of the container, whereby the container axis is substantially coaxial with the central axis and the aerosol valve is positioned adjacent the shoulder and in communication with the expulsion nozzle. The device further includes a diaphragm assembly having a relatively rigid central disk, a peripheral attachment ring disposed about a peripheral portion of the disk, and an annular flexure extending between the peripheral portion of the disk and the attachment ring. The central disk is affixed to the first end of the housing and the peripheral ring is affixed to the sleeve, thereby defining a closed region between the diaphragm and the sleeve. A breath actuated valve assembly is provided to selectively establish in a first state an air flow path between the closed region and regions exterior thereto, and interrupting in a second state the air flow path. A spring force bias element is adapted to bias the sleeve toward the second end of the housing. When the breath actuated valve element is in the second state, pneumatic pressure in the closed region establishes a force on the sleeve opposite the bias. In that circumstance, the axial force on the aerosol valve is below the predetermined threshold, and whereby when the breath actuated valve element is in the first state, pneumatic pressure in the closed region establishes a substantially zero force on the sleeve and the bias is sufficient to drive the sleeve and the container toward the shoulder and establish an axial force on the aerosol valve above the predetermined threshold.

Preferably, the central disk is made of a first material characterized by a relatively high stiffness, and the annular flexure is made of a second material characterized by a relatively low stiffness. The annular flexure is bonded to the disk, whereby the disk, the annular flexure and the peripheral ring form a contiguous assembly. In an alternative form, the ring and flexure may be different material as well. Preferably, the multimaterial diaphragm is made using a multishot molding process wherein a first portion (such as the disk) is molded in a first step, and a second portion (such as the flexure and ring) molded in a second step, and at the same time bonded to the first portion.

It is also preferred that the release device is breath-actuated in order to co-ordinate the release of the medicament with the intake of breath. The favored breath-actuating means comprises a moveable vane mechanism. This vane mechanism may be housed in the upper part of the chamber. A valve seal is preferably attached to said vane, such that on inhalation the vane moves from its rest position to its actuating position, thus moving the valve seal out of contact with the valve port, causing the opening of the valve. The vane mechanism is preferably biased towards its closed position, e.g., by a spring. When the valve opens, an air flow path is established between the negative pressure region and regions exterior thereto.

The outer chamber may include air inlets allowing passage of air to the mouthpiece of the device. The inlets may take the form of slots or of an air porous membrane. The latter is particularly suitable to help filter dust.

The medicament may be a drug per se or on any form of carrier, e.g. including a powder or a gaseous carrier.

BRIEF DESCRIPTION OF THE DRAWINGS

For a fuller understanding of the nature and the objects of the invention, reference should be made to the following detailed description and the accompanying drawings in which like reference numerals refer to like elements and in which:

FIG. 1 is a section view of an inhaler according to an embodiment of the invention;

FIG. 2 shows an enlarged view of a diaphragm for use with the embodiment shown in FIG. 1; and FIG. 3 shows an enlarged section view of the diaphragm in position in pre-actuated and actuated state.

DESCRIPTION OF THE PREFERRED EMBODIMENT

In an arrangement as shown in FIG. 1, an inhalation device consists of a main body 400 which is generally cylindrical in cross section, with a mouthpiece section 405 at one end and an end cap 407 housing air inlets 420 at the other end. A known type of aerosol dispensing container 25 of generally cylindrical shape is housed within the main body of the device. The aerosol dispensing container has a stem 40 which contains an aerosol dispensing valve (not shown). The bore 15 is such that it forms an air tight seal on the stem 40 of the aerosol dispensing container 25. A shoulder 45 limits and locates the position of the stem 40, which in turn locates the aerosol dispensing container 25 in position in the main body 400. A passage 50 extends from the bore 15, continuing from the shoulder 45 to interconnect with a dispensing nozzle 55.

The opposite end of the dispensing container is contained within a sleeve 420 of similar cross section to the main body 400. The longitudinal axis of both the sleeve 420 and main body 400 is generally coaxial. The sleeve is in loose sliding contact with the inner wall of the main body and may include several rebated grooves 430 in its walls to allow free passage of air in the main body past the sleeve. The sleeve 420 may be held in place by connection with a diaphragm 440 held in connection with the top of the main body 400, as will now be described. Thus, the sleeve 420 effectively hangs from the top of the main body.

One end of an e.g., moulded flexible diaphragm 440 (as shown alone in FIG. 2) comprising a rigid disc-like section 441, a flexible generally cylindrical wall section 445 and a stiffer connector section 447, is fitted around a purpose-made groove 450 in the sleeve, e.g., by snap-fitting. A further moulded lip 470 on the diaphragm provides a snug fit for one end of a compression spring 460. The compression spring is thus located and free to act on the sleeve. The other end of the compression spring is located by an annular shoulder 481 in a predominantly cylindrical flanged insert 480 housed in the top section of the main body 400. This insert includes a groove 490 into which the disc-like section 441 of the flexible diaphragm 440 is snap-fitted. Preferably, the multimaterial diaphragm is made using a multishot molding process wherein a first portion (such as the disk) is molded in a first step, and a second portion (such as the flexure and ring) re molded in a second step, and at the same time bonded to the first portion.

With the improved diaphragm configuration of the invention, shown in FIG. 2, the relatively thick disk-portion A is molded from a rigid material (relatively high stiffness), which is particularly resistant to flexural deformation when the closed region 600 is at negative pressure, while the relatively thin flexure portion B is molded from an optimally flexible (relatively low stiffness) material, permitting high performance. The use of a rigid material for the disk portion of the diaphragm allows the section's thickness to be reduced without compromising stiffness of the disk portion, thus substantially reducing the molding cycle time required. One of skill in the art will appreciate that the use of equal sections in a component facilitates optimization and increases the efficiency of the molding process. The diaphragm according to the invention is produced in a two-shot molding process with the disk being molded first, and then the flexure, so that the inner portion of the flexure is adjacent, and bonds to, the peripheral portion of the central disk. Alternative methods, such as compression molding of the flexure onto a rigid insert using vulcanizing materials, or casting of a silicone rubber onto a rigid insert may also be used. In preferred embodiments of the invention, the flexure of the diaphragm 440 is made of an elastic polymer, preferably a thermoplastic elastomer, including extrusion grade thermoplastic elastomers such as for example, ELASTOLAN™, SANTOPRENE™, EVOPRENE™ (commercially available from BASF). Semirigid elastomers of sufficient flexibility, such as low molecular weight polyethylene may also be used. The inventors have made the surprising discovery that materials typically used for extrusion molding applications are suitable for the production of the diaphragm by injection molding. The diaphragm according to the invention has a thickness from about 0.1 mm to about 0.5 mm, preferably from about 0.2 mm to about 0.4 mm, more preferably of about 0.3 mm. The diameter of the diaphragm may vary to address the specific requirements in a given application. One of skill will appreciate that the force that can be withheld by a vacuum is proportional to the area over which it acts. For example, in preferred embodiments a diaphragm of effective diameter of 22.5 mm will generate a restraining force of approximately 40 Newtons when there is a pressure difference of 1 std. Atmosphere.

The joint between the diaphragm connector section 447 and inner sleeve groove 450 is arranged to be air tight and the shape of the top surface of the sleeve 422 to conform to the internal shape of the diaphragm such that in the rest position of the inhaler the two surfaces are in close proximity, and the enclosed space between them very small.

The cylindrical insert 480 is retained in place by the end cap 407 fitted into the main body of the device. This forms a chamber 590 between the air inlet slots 420 and the rigid part 441 of the diaphragm. The chamber is provided with one or more air pathways 580 such that air may pass from the air inlet slots 420 to the mouthpiece 405. The rigid disc-like section 441 of the diaphragm also includes a small valve port 495 which is normally covered by a valve seal (flap) 540 housed in a vane 550 pivotally connected to the insert 480.

The vane 550 in its rest position divides the chamber 590 between the air inlets 420 and the air pathways 580 that link to the mouthpiece such that it may move from its rest position by means of a pressure drop between the air inlets and the mouthpiece. On movement of the vane to the actuated position the valve seal (flap) 540 is sufficiently moved to open the valve port 495. (The vane 550 may be biased closed by a light spring flexure, a weight or a magnet not shown).

As shown in FIG. 1, the end of the main body having a pivot 500 has a recess adapted to receive a cam 520 integral with a dust cap 510 operating on the pivot. The recess further includes a passage communicating with a similar passage moulded into the internal wall of the main body 400. A camfollower 530 extending from the lower edge of the inner sleeve 421 acts on the cam such that when the dust cap is in the closed position the inner sleeve is forced by the camfollower to its uppermost position.

When the dust cap is rotated to its open position the cam profile is such that the camfollower is free to move downwards by an amount sufficient to allow actuation of the device.

In its rest position the dust cap 510 is closed, the cam follower 530 restrains the inner sleeve 420 in its uppermost position such that the enclosed space trapped between the diaphragm 440 and the top surface 422 of the inner sleeve is at a minimum and the spring 460 is compressed. The valve port 495 is closed by the valve seal (flap) 540 and the sleeve 421 is clear of the top of the aerosol can 25 which is thus unloaded.

Figure 3:
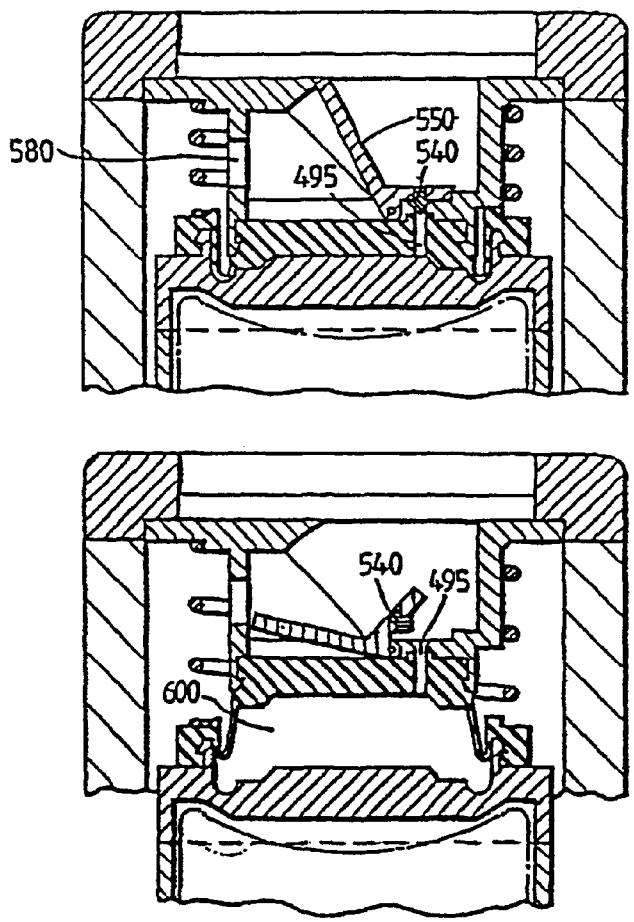

The dust cap is opened rotating the integral cam 520 allowing the camfollower 530 to drop by amount AA. The inner sleeve is forced downwards under the action of the spring 460. As the inner sleeve moves downwards the enclosed volume between the diaphragm 440 and the inner sleeve is increased by a linear equivalent amount A'A', less than or equal to AA. Since the valve port 495 is closed this creates a low pressure volume or near vacuum in the space 600 [FIG. 3]. The effect of the pressure differential between the enclosed volume 600 and atmospheric pressure is such that the inner sleeve tends to resist the action of the spring. As the inner sleeve moves downwards it contacts the aerosol can 25 and begins compression of the aerosol valve (not shown).

Downward movement of the inner sleeve will continue until there is a balance of forces between the compressive force in the spring 460 and resisting forces created by the pressure differential and compression of the aerosol valve. The geometry of the device is arranged such that this balance occurs before the aerosol valve has been sufficiently compressed to actuate it.

A typical aerosol requires from about 20 to 30 Newtons force to actuate. The spring 460 should accordingly provide a greater force, preferably 10% to 50% greater.

It may also be possible to arrange for the balance of forces to take place before the inner sleeve has contacted the aerosol can, such that the spring force is balanced by the resisting force produced on the inner sleeve by virtue of the pressure differential.

On inhalation by the patient through the mouthpiece 405, a small pressure differential is created across the vane 550 which is pivoted towards one end. The pressure differential causes the vane to move from the rest position to the actuated position. The vane and design of the air passageway 580 in the chamber 590 are such that in the actuated position air can flow freely from the air inlets 420 to the patient.

The movement of the vane 550 causes the valve seal (flap) 540 to be moved out of a sealing position with the valve port 495. Opening the valve port allows air into the gap 600 between the diaphragm and inner sleeve such that the enclosed space reaches atmospheric pressure. This causes an imbalance of forces acting on the sleeve 420 and container 25. The sleeve and container are thus forced downwards by the spring 460 resulting in the release of a measured dose of medicament through the dispensing nozzle 55 and into the mouthpiece at the same time as the patient breathes in. Thus the patient inhales air with a metered dose of medicament.

After the inhalation of the dose by the patient, the dust cap 510 is returned to its closed position. This rotates the cam 520 and causes the camfollower 530 to be forced upwards. This in turn acts on the inner sleeve 420 moving it upwards to compress the spring 460 and close the gap 600 between the diaphragm and inner sleeve top surface 422. This forces air out of the enclosed space 600 which escapes through the valve port 495 lifting the valve seal (flap) 540. Since the valve seal (flap) is only lightly biased to its closed position it presents little resistance to air flow out of the enclosed space. The aerosol can is free to return to the rest position under the action of its own aerosol valve spring.

In use the patient loads the aerosol dispensing container into the main body. The aerosol container may be loaded by providing a coarse threaded screw in the main body 400, for example about the line I—I. When part of the main body 400 has been unscrewed, the aerosol can be inserted. The main body 400 can then be replaced locating the inner sleeve over the top end of the can, and the device is ready for use. As described previously, the device could be manufactured as a sealed unit.

The device may be provided with means to provide a regulated air flow to the user or inhaler. Thus a sonic device, e.g., a reed, may be provided which sounds when the inspired air flow is greater than a pre-set level, e.g., above 30 to 50 liters per minute. The sonic device may be located in the mouthpiece 95 or below the air inlet 420. The sound produced warns the patient to breathe at a lower rate.

The device may also be provided with a means such that it will not operate below a certain pre-determined air flow rate, e.g., 10 to 30 liters per minute. In one embodiment the vane 550 or 110 will be biased by a spring such that the predetermined minimum air flow is necessary for it to move to its actuated position and enable the valve seal to open.

The main body of a dispensing device, as described in the above embodiment of this invention is preferably manufactured from a plastic such as polypropylene, acetal or moulded polystyrene. It may however be manufactured from metal or another suitable material The invention may be embodied in other specific forms without departing from the spirit or essential characteristics thereof. The present embodiments are therefore to be considered in all respects illustrative and not restrictive, the scope of the invention being indicated by the appended claims rather than by the foregoing description, and all changes which come within the meaning and range of equivalency of the claims are therefore intended to be embraced therein.

What is claimed is:

1. A breath actuated dispensing device for dispensing a medicant in a metered dose from an aerosol medicament container, said container being cylindrical and extending along a container axis between a first end and a second end, said container having a spring based aerosol valve at said first end responsive to an axial force above a predetermined threshold to release said metered dose, comprising:

A. a housing disposed about a central axis and having a first end and a second end, said second end including a shoulder and an expulsion nozzle extending therethrough;

B. a support sleeve disposed within said housing said sleeve being adapted for axial motion along said central axis, and being adapted to support said second end of said container whereby said container axis is substantially coaxial with said central axis and said aerosol valve is positioned adjacent said shoulder and in communication with said expulsion nozzle;

C. a diaphragm assembly including a relatively rigid central disk, a peripheral attachment ring disposed about a peripheral portion of said disk, and an annular flexure extending between said peripheral portion of said disk and said peripheral attachment ring, wherein said central disk is affixed to said first end of said housing and said peripheral attachment ring is affixed to said sleeve, thereby defining a closed region between said diaphragm and said sleeve;

D. a breath actuated valve assembly adapted to selectively establish in a first state an air flow path between said closed region and regions exterior thereto, and interrupting in a second state said air flow path;

E. a spring force bias element adapted to bias said sleeve toward said second end of said housing whereby when said breath actuated valve element is in said second state, pneumatic pressure in said closed region establishes a force on said sleeve equal to and opposite said bias whereby said axial force on said aerosol valve is below said predetermined threshold, and whereby when said breath actuated valve element is in said first state, pneumatic pressure in said closed region establishes a zero force on said sleeve and said bias is sufficient to drive said sleeve and said container toward said shoulder and establish an axial force on said aerosol valve above said predetermined threshold, wherein said central disk is made of a first material characterized by a relatively high stiffness, and said annular flexure is made of a second material characterized by a relatively low stiffness, and wherein said annular flexure is bonded to said disk, wherein the first material differs from the second material, whereby said disk, said annual flexure and said peripheral attachment ring form a contiguous assembly.

2. A dispensing device according to claim 1, wherein said peripheral ring is made of said second material.

3. A dispensing device, for use with an aerosol medicament container, for dispensing a medicant in metered doses comprising:

a main body with a first and second end;

a sleeve comprising sides and a base;

a diaphragm assembly comprising a valve port operationally connected to said second end of said main body and said base of said sleeve;

a spring operationally positioned in said second end of said main body so as to apply a preload force to said sleeve; and a vane operationally attached to said diaphragm wherein said vane has first and second positions, wherein when said vane is in said first position said vane seals said valve port and when said vane is in said second position said valve port is unsealed; wherein diaphragm assembly includes a relatively rigid central disk, a peripheral attachment ring disposed about a peripheral portion of said disk, and an annular flexure extending between said peripheral portion of said disk and said peripheral attachment ring, wherein said central disk is affixed to said first end of said main body and said peripheral attachment ring is affixed to said sleeve, thereby defining a closed region between said diaphragm and said sleeve; and wherein said central disk is made of a first material characterized by a relatively high stiffness, and said annular flexure is made of a second material characterized by a relatively low stiffness, and wherein said annular flexure is bonded to said disk, wherein the first material differs from the second material, whereby said disk, said annular flexure and said peripheral attachment ring form a contiguous assembly.

4. A dispensing device as claimed in claim 3, further comprising air inlets disposed in said second end of said main body.

5. A dispensing device as claimed in claim 3, further comprising a mouthpiece integrally formed in said first end of said main body.

6. A dispensing device as claimed in claim 3, further comprising:

a dust cap pivotally attached to said first end of said main body capable of covering said mouthpiece wherein said dust cap comprises a cam; and a cam follower disposed in said main body and operationally connected between said cam and said sleeve.

7. A dispensing device comprising:

a drug delivery system comprising a dispensing container capable of dispensing a metered dose;

a main body;

a releasing means for releasing a metered dose;

a sleeve within said main body and capable of receiving said dispensing container;

wherein said releasing means comprises a means for applying a preload force to said sleeve and capable of actuating said container in said system, a preventative force means for applying a resisting pneumatic force to said sleeve capable of preventing actuation of said container, and a release device capable of freeing said resisting pneumatic force to actuate said delivery system and dispense said metered dose;

wherein said preventive force means includes a relatively rigid central disk, a peripheral attachment ring disposed about a peripheral portion of said disk, and an annular flexure extending between said peripheral portion of said disk and said peripheral attachment ring, wherein said central disk is affixed to said main body and said peripheral attachment ring is affixed to said sleeve, thereby defining a closed region between said diaphragm and said sleeve; and wherein said central disk is made of a first material characterized by a relatively high stiffness, and said annular flexure is made of a second material characterized by a relatively low stiffness, and wherein said annular flexure is bonded to said disk, wherein the first material differs from the second material, whereby said disk, said annular flexure and said peripheral attachment ring form a contiguous assembly.

* * * * *